(12) United States Patent
MacPhee et al.

(10) Patent No.: US 8,679,528 B2
(45) Date of Patent: Mar. 25, 2014

(54) HEMOSTATIC DRESSING

(71) Applicants: Martin J. MacPhee, Gaithersburg, MD (US); Dawson Beall, Gaithersburg, MD (US); Stanley Friedman, Burtonsville, MD (US)

(72) Inventors: Martin J. MacPhee, Gaithersburg, MD (US); Dawson Beall, Gaithersburg, MD (US); Stanley Friedman, Burtonsville, MD (US)

(73) Assignee: American National Red Cross, Rockville, MD (US)

( * ) Notice: Subject to any disclaimer, the term of this patent is extended or adjusted under 35 U.S.C. 154(b) by 0 days.

(21) Appl. No.: 13/630,890

(22) Filed: Sep. 28, 2012

(65) Prior Publication Data

US 2013/0028954 A1 Jan. 31, 2013

Related U.S. Application Data

(63) Continuation of application No. 10/525,415, filed as application No. PCT/US03/28100 on Sep. 9, 2003, now abandoned.

(60) Provisional application No. 60/409,212, filed on Sep. 10, 2002.

(51) Int. Cl.
*A61L 15/32* (2006.01)
*A61F 13/02* (2006.01)

(52) U.S. Cl.
USPC ............. 424/447; 602/48; 514/1.1; 514/9.4; 424/443; 424/444; 424/445; 424/446

(58) Field of Classification Search
USPC ................ 424/443–449; 602/54–58
See application file for complete search history.

(56) References Cited

U.S. PATENT DOCUMENTS

| | | | |
|---|---|---|---|
| 2,533,004 A | 12/1950 | Ferry et al. | |
| 3,089,815 A | 5/1963 | Lieb et al. | |
| 3,523,807 A | 8/1970 | Gerendas | |
| 3,723,244 A | 3/1973 | Breillatt, Jr. | |
| 4,265,233 A | 5/1981 | Sugitachi et al. | |
| 4,298,598 A | 11/1981 | Schwarz et al. | |
| 4,321,711 A | 3/1982 | Mano | |
| 4,359,049 A | 11/1982 | Redl et al. | |
| 4,362,567 A | 12/1982 | Schwarz et al. | |
| 4,373,519 A | 2/1983 | Errede et al. | |
| 4,377,159 A | 3/1983 | Hansen | |
| 4,377,572 A | 3/1983 | Schwarz et al. | |
| 4,393,041 A | 7/1983 | Brown et al. | |
| 4,394,370 A | 7/1983 | Jefferies | |
| 4,407,787 A | 10/1983 | Stemberger | |
| 4,414,976 A | 11/1983 | Schwarz et al. | |
| 4,427,650 A | 1/1984 | Stroetmann | |
| 4,427,651 A | 1/1984 | Stroetmann | |
| 4,442,655 A | 4/1984 | Stroetmann | |
| 4,453,939 A | 6/1984 | Zimmerman et al. | |
| 4,472,840 A | 9/1984 | Jefferies | |
| 4,516,276 A | 5/1985 | Mittelmeier et al. | |
| 4,548,763 A | 10/1985 | Nalewajek et al. | |
| 4,597,960 A | 7/1986 | Cohen | |
| 4,600,574 A | 7/1986 | Lindner et al. | |
| 4,606,337 A | 8/1986 | Zimmermann et al. | |
| 4,617,293 A | 10/1986 | Wahlig et al. | |
| 4,619,913 A | 10/1986 | Luck et al. | |
| 4,619,989 A | 10/1986 | Urist | |
| 4,627,879 A | 12/1986 | Rose et al. | |
| 4,631,055 A | 12/1986 | Redl et al. | |
| 4,642,120 A | 2/1987 | Nevo et al. | |
| 4,714,457 A | 12/1987 | Alterbaum | |
| 4,717,717 A | 1/1988 | Finkenaur | |
| 4,761,471 A | 8/1988 | Urist | |
| 4,789,732 A | 12/1988 | Urist | |
| 4,816,339 A | 3/1989 | Tu et al. | |
| 4,820,626 A | 4/1989 | Williams et al. | |
| 4,837,379 A | 6/1989 | Weinberg | |
| 4,861,757 A | 8/1989 | Antoniades et al. | |
| 4,874,746 A | 10/1989 | Antoniades et al. | |
| 4,909,251 A | 3/1990 | Seelich | |
| 4,928,603 A | 5/1990 | Rose et al. | |
| 4,952,403 A | 8/1990 | Vallee et al. | |
| RE33,375 E | 10/1990 | Luck et al. | |
| 4,969,880 A | 11/1990 | Zamierowski | |
| 4,983,581 A | 1/1991 | Antoniades et al. | |
| 4,997,425 A | 3/1991 | Shioya et al. | |
| 5,019,559 A | 5/1991 | Antoniades et al. | |
| 5,023,082 A | 6/1991 | Friedman et al. | |
| 5,024,742 A | 6/1991 | Nesburn et al. | |

(Continued)

FOREIGN PATENT DOCUMENTS

AU   B-83581/82   11/1982
AU   B-43122/85   12/1985

(Continued)

OTHER PUBLICATIONS

Supplemental European Search Report for European Application No. EP 03 75 2091, completed Jan. 20, 2009, The Hague, The Netherlands.

(Continued)

*Primary Examiner* — Lakshmi Channavajjala

(74) *Attorney, Agent, or Firm* — Sterne, Kessler, Goldstein and Fox P.L.L.C.

(57) ABSTRACT

The present invention relates to a hemostatic dressing which comprises a plurality of layers that contain resorbable materials and/or coagulation proteins. In particular, the invention includes dressings in which a layer of thrombin is sandwiched between a first and second layer of fibrinogen and wherein the layer of thrombin is not coextensive with the first and/or second layer of fibrinogen. The hemostatic dressings are useful for the treatment of wounded tissue.

16 Claims, No Drawings

(56) References Cited

U.S. PATENT DOCUMENTS

| | | | |
|---|---|---|---|
| 5,030,215 | A | 7/1991 | Morse et al. |
| 5,034,375 | A | 7/1991 | Antoniades et al. |
| 5,035,887 | A | 7/1991 | Antoniades et al. |
| 5,059,123 | A | 10/1991 | Jernberg |
| 5,100,396 | A | 3/1992 | Zamierowski |
| 5,124,155 | A | 6/1992 | Reich |
| 5,139,527 | A | 8/1992 | Redl et al. |
| 5,171,318 | A | 12/1992 | Gibson et al. |
| 5,171,579 | A | 12/1992 | Ron et al. |
| 5,206,023 | A | 4/1993 | Hunziker |
| 5,219,328 | A | 6/1993 | Morse et al. |
| 5,226,877 | A | 7/1993 | Epstein |
| 5,290,552 | A | 3/1994 | Sierra et al. |
| 5,294,314 | A | 3/1994 | Nesburn et al. |
| 5,368,858 | A | 11/1994 | Hunziker |
| 5,431,790 | A | 7/1995 | Nesburn et al. |
| 5,702,715 | A | 12/1997 | Nikolaychik et al. |
| 5,763,411 | A | 6/1998 | Edwardson et al. |
| 6,054,122 | A | 4/2000 | MacPhee et al. |
| 6,117,425 | A | 9/2000 | MacPhee et al. |
| 6,124,273 | A | 9/2000 | Drohan et al. |
| 6,197,325 | B1 | 3/2001 | MacPhee et al. |
| 6,762,336 | B1 | 7/2004 | MacPhee et al. |
| 6,893,655 | B2 | 5/2005 | Flanigan et al. |
| 7,189,410 | B1 | 3/2007 | Drohan et al. |
| 2006/0179793 | A1 | 8/2006 | Yewdall et al. |

FOREIGN PATENT DOCUMENTS

| | | |
|---|---|---|
| AU | B-75097/87 | 1/1988 |
| CA | 1119516 | 3/1982 |
| CA | 1 168 982 A | 6/1984 |
| DE | 3037270 | 5/1982 |
| EP | 0 081 990 A1 | 6/1983 |
| EP | 0 090 997 A2 | 10/1983 |
| EP | 0 312 208 A1 | 4/1989 |
| EP | 0 443 724 A1 | 8/1991 |
| EP | 0 485 210 A2 | 5/1992 |
| EP | 0 562 864 A1 | 9/1993 |
| EP | 0 919 211 A2 | 6/1999 |
| GB | 2 041 942 | 9/1980 |
| GB | 2 042 556 A | 9/1980 |
| GB | 1 584 080 | 2/1981 |
| GB | 2 102 811 A | 2/1983 |
| GB | 2 137 209 A | 10/1984 |
| GB | 2 185 747 A | 7/1987 |
| JP | 54-104687 A | 8/1979 |
| JP | 60-204725 A | 10/1985 |
| JP | 62-246370 A | 10/1987 |
| JP | 63-115564 A | 5/1988 |
| JP | A H04-370262 | 12/1992 |
| JP | A H08-175981 | 7/1996 |
| JP | A H08-231386 | 9/1996 |
| WO | WO 81/00516 A1 | 3/1981 |
| WO | WO 86/00526 A1 | 1/1986 |
| WO | WO 86/01814 A1 | 3/1986 |
| WO | WO 86/03122 A1 | 6/1986 |
| WO | WO 91/09573 A1 | 7/1991 |
| WO | WO 91/17744 A1 | 11/1991 |
| WO | WO 92/09301 A1 | 6/1992 |
| WO | WO 92/09697 A1 | 6/1992 |
| WO | WO 92/13565 A1 | 8/1992 |
| WO | WO 92/22312 A1 | 12/1992 |
| WO | WO 93/05067 A1 | 3/1993 |
| WO | WO 94/20133 | 9/1994 |
| WO | WO 97/28832 | 8/1997 |
| WO | WO 99/59647 A1 | 11/1999 |

OTHER PUBLICATIONS

Unverified English language abstract of JP-A (Kokai) H04-370262, Dec. 1992.
Unverified computer English language translation of JP-A (Kokai) H08-175981, Jul. 1996.
Unverified computer English language translation of JP-A (Kokai) H08-231386, Sep. 1996.
Unverified English language translation of Notice of Reasons for Rejection, issued on Feb. 8, 2010 in Japanese Patent Application No. 2004-536153.
Achauer, B.M., et al., "The Hemostatic Effect of Fibrin Glue on Graft Donor Sites," *J. Burn Care Rehabil.* 15:24-28, Burn Science Publishers. Inc, (1994).
Adelmann-Grill, B.C., et al., "Chemotactic migration of normal dermal fibroblasts towards epidermal growth factor and its modulation by platelet-derived growth factor and transforming growth factor-beta," *Eur. J. Cell. Biol.* 51:322-326, Wissenschaftliche Verlaosgesellscheft mbH (1990).
Afra. D., et al., "Experimentelle Untersuchung der Resorption von Fibrinfilmen und ihre Anwendung in der neurochirurgischen Praxis", *Acta Med. Acad. Sci. Hung.* 11:1-29, Hungarian Academy of Sciences (1958).
Akrami, R., et al., "Replacement of the Thoracic Aorta by Sealed Dacron Prostheses," *Thoraxchirurgie* 26:144-147, Georg Thieme Verlag Stuttgart (1978).
Albrektsson, T., et al., "Fibrin Adhesive System (FAS) Influence on Bone Healing Rate," *Acta Orthop. Scand.* 53:757-763, Munksgaard (1982).
Allen, B.T., et al., "Influence of endothelial cell seeding on platelet deposition and patency in small-diameter Dacron arterial grafts," *J. Vasc. Surg. 1*:224-233, Mosby-Year Book Inc.(1984).
Alving, B.M., et al., "Fibrin sealant: summary of a conference on characteristics and clinical uses," *Transfusion* 35:783-790, The American Association of Blood Banks (1995).
Andreassen, T,T., and Jorgensen, P.H., "Biomechanical Properties and Collagen Formation in Subcutaneously Implanted Cellulose Sponges Treated with Fibrin Sealant," *Eur. surg. Res.* 17:264-268, S.Karger AG (1985).
Arbes, H., et al., "First Clinical Experience with Heterologous Cancellous Bone Grafting Combined with the Fibrin Adhesive System (F.A.S.)," *Arch. Orthop. Traumat. Surg.* 98:183-188, J.F. Bergmann Verlag (1981).
Bagdy, D., et al., "Application of Bovine Fibrin Foam and of a Mixture of Thrombin and Fibrin Powders as Haemostatic Agents," *Acta. Physiol. Acad. Sci. Hung.* 2:493-504, Magyar Tudományos Akadémia (1951).
Bagdy, D., et al., "Experimentelle und klinische Anwendung der aus Rinderplasma hergestellten Fibrinprodukte," *Zentralblett für Chirurgie* 77:848-852. Vereinigung Mittelrheinischer Chirurgen (1952).
Bagdy, D., et al., "Die klinische Anwendung von Thrombin-Fibrinpulver. Die Anwendung von Fibrinfilm und Fibrinröhren bei peripheren Nervennähten," in *Trombin-Fibrinprodukte und ihre Therapeutische Anwendung*, Veb Gustav Fischer Verlag Jena, Germany, pp. 152-169, pp. 184-187 (1963).
Bailey, O.T., and Ingraham, F.D., "Chemical, Clinical, and Immunological Studies on the Products of Human Plasma Fractionation. XXI. The Use of Fibrin Foam as Hemostatic Agent in Neurosurgery: Clinical and Pathological Studies," *J. Clin. Invest.* 23:591-595, The American Society for Clinical Investigation (1944).
Bailey, O.T., and Ingraham, F.D., "Chemical, Clinical, and Immunological Studies on the Products of Human Plasma Fractionation. XXII. Fibrin Films in Neurosurgery, with Special Reference to Their Use in the Repair of Dural Defects and in the Prevention of Meningocerebral Adhesions," *J. Clin. Invest.* 23:597-600, The American Society for Clinical Investigation (1944).
Bailey, O.T., et al., "Fibrin Film in Neurosurgery, Further Studies: The Insertion of Fibrin Film Between the Sutured Dura and the Intact Leptomeninges; The Effect of Roentgen Therapy on Tissue Reactions to Fibrin Film," *J. Neurosurg.* 4:465-471, American Association of Neurological Surgeons (1947).
Baird, A., and Walicke, P.A., "Fibroblast growth factors," *Brit. Med. Bull..* 45:438-452, The British Council(1989).
Berger, K., et al., "Healing of Arterial Prostheses in Man: Its Incompleteness," *Ann. Surg.* 175:118-127, J.B. Lippincott Company (1972).

(56) References Cited

OTHER PUBLICATIONS

Bishara, S.E., et al., "Effects of a Fibrin-Sealant Wound Dressing on the Healing of Full-Thickness Wounds of the Hard Palate: Preliminary Report," *Cleft Palate J.* 23:144-152, Allen Press Inc. (1986).
Bösch, P., et al., "Die Technik der Firbrinspongiosaplastik," *Orthop. Unfall-Chir.* 90:63-75, J.F. Bergmann-Verlag (1977).
Bösch, P., et al., "Die autologe Spongiosatransplantation unter Anwendung des Fibrinklebesystems im Tierexperiment," *Wiener klinische Wochenschrift* 91:628-634, Springer-Verlag Wien (1979).
Bösch, P., "Experimental Investigations of the Effect of the Fibrin Adhesive on the Kiel Heterologous Bone Graft," *Arch. Orthop. Traumat. Surg.* 96:177-185, J.F. Bergmann Verlag (1980).
Bösch, P., "Die Fibrinspongiosaplastik," *Weiner klinische Wochenschrift* 93:3-26, Springer-Verlag Wien (1981).
Borst, H.G., et al., "Fibrin adhesive: An important hemostatic adjunct in cardiovascular operations," *J. Thorac. Cardiovasc. Surg.* 84:548-553, The C.V. Mosby Co. (1982).
Brown, D.M., et al., "Decreased Wound Contraction With Fibrin Glue-Treated Skin Grafts," *Arch. Surg.* 127:404-406, American Medical Association (1992).
Burgess, W.H. and Maciag, T., "The Heparin-Binding (Fibroblast) Growth Factor Family of Proteins," *Annu. Rev. Biochem.* 58:575-606, Annual Reviews Inc. (1989).
Byrne, D.J., et al., "Effect of fibrin glues on the mechanical properties of healing wounds," *Br. J. Surg.* 78:841-843, Butterworth-Heinemann Ltd. (1991).
Carter, D.M., et al., "Clinical Experience with Crude Preparations of Growth Factors in Healing of Chronic Wounds in Human Subjects," in *Growth Factors and Other Aspects of Wound Healing: Biological and Clinical Implications*, Alan R. Liss, Inc., pp. 303-317 (1988).
Clark, A.M., et al., "Fixation of Skin-Grafts with Human Plasma and Thrombin," *Lancet* 1:498-500, The Lancet Ltd. (1945).
Clowes, A.W., and Kohler, T., "Graft Endothelialization: The Role of Angiogenic Mechanisms," *J. Vasc. Surg.* 13:734-736, Mosby-Year Book, Inc. (1991).
Clowes, A.W., et al., "Mechanisms of Arterial Graft Healing. Rapid Transmural Capillary Ingrowth Provides a Source of Intimal Endothelium and Smooth Muscle in Porous PTFE Prostheses," *Am. J. Pathol.* 123:220-230, American Society of Investigative Pathology (1986).
Conant, M., et al., "Treatment of Condylomata Acuminate with Intralesional 5-Fluorouracil Tnerapeutic Implant (MPI 5003)," *Clinical Res.* 39:818A, The American Federation for Clinical Research (1991).
Cronkite, E.P., et al., "Use of Thrombin and Fibrinogen in Skin Grafting: Preliminary Report," *J.A.M.A.* 124:976-978, The American Medical Association (1944).
Davidson, J. et al., "Mechanisms of Accelerated Wound Repair Using Epidermal Growth Factor and Basic Fibroblast Growth Factor," in *Growth Factors and Other Aspects of Wound Healing: Biological and Clinical Implications*, Alan R. Liss, Inc., pp. 63-75 (1988).
Dees, J.E., "The Use of an Intrapelvic Coagulum in Pyelolithotomy: Preliminary Report," *South. Med. J.* 36:167-175, The Southern Medical Association (1943).
Dees, J.E., and Fox, H., "The Properties of Human Fibrinogen Coagulum—Preliminary Report," *J. Urol.* 49:503-511, The Williams & Wilkins Company (1943).
Dees, J.E., "Chemical, Clinical, and Immunological Studies on the Products of Human Plasma Fractionation. XVIII. Fibrinogen Coagulum as an Aid in the Operative Removal of Renal Calculi," *J. Clin. Invest.* 23:576-579, The American Society for Clinical Investigation (1944).
Dees, J.E., "The Use of a Fibrinogen Coagulum in Pyelolithotomy," *J. Urol.* 56:271-283, The Williams & Wilkins Company (1946).
Deyerling, W., et al., "A Suspension of Fibrin Glue and Antibiotic for Local Treatment of Myocotic Aneurysms in Endocarditis—An Experimental Study," *Thorac. cardiovasc. Surgeon* 32:369-372, Georg Thieme Verlag Stuttgart (1984).
English translation of the fourth-eighth paragraphs on p. 479 of Winter, L, et al., "Experimentelle und klinische Anwendung der aus Rinderplasma hergestellten Fibrinprodukte. III. Klinische Verwendung von hämostatischen Fibrinprodukten," *Zentralblatt für Chirurgie* 78:469-479, Vereinigung Mittelrheinischer Chirurgen (1953), translated by McElroy Translation Company (dated Aug. 24, 2001).
Dresdale, A., et al., "Hemostatic Effectiveness of Fibrin Glue Derived from Single-Donor Fresh Frozen Plasma," *Ann. Thorac Surg.* 40:385-387, The Society of Thoracic Surgeons (1985).
Dresdale, A. et al., "Preparation of fibrin glue from single-donor fresh-frozen plasma," *Surgery* 97:750-755, Mosby-Year Book, Inc. (1985).
Durham, L.H., et al., "A method for preparation of fibrin glue," *J. Laryngol. Otol.* 101:1182-1186, Headley Brothers Ltd. (1987).
Dvorak, H.F., et al., "Fibrin Containing Gels Induce Angiogenesis. Implications for Tumor Stroma Generation and Wound Healing," *Lab. Invest.* 57:673-686, The United States and Canadian Academy of Pathology, Inc. (1987).
Epstein, G.H., et al., "A New Autologous Fibrinogen-Based Adhesive for Otologic Surgery," *Ann. Otol. Rhinol. Laryngol.* 95:40-45, Annals Publishing Company (1986).
Ferry, J.D., and Morrison, P.R., "Chemical, Clinical, and Immunological Studies on the Products of Human Plasma Fractionation. XVI. Fibrin Clots, Fibrin Films, and Fibrinogen Plastics," *J. Clin. Invest.* 23:566-572, The American Society for Clinical Investigation (1944).
Foxall, T.L., et al., "Adult Human Endothelial Cell Coverage of Small-Caliber Dacron and Polytetrafluoroethylene Vascular Prostheses in Vitro," *J. Surg, Res.* 41:158-172, Academic Press, Inc.(1986).
Froesch, E.R., et al., "Actions of Insulin-Like Growth Factors," *Ann. Rev. Physiol.* 47:443-467, Annual Reviews, Inc.(1985).
Frucht-Perry, J,. et al., "Fibrin-Enmeshed Tobramycin Liposomes: Single Application Topical Therapy of *Pseudomonas keratitis*," *Cornea* 11:393-397, Raven Press, Ltd. (1992).
Gerendás, M., "Fibrin Products as Aids in Hemostasis and Wound Healing," in *Fibrinogen*, Chapter 13, Laki, K., Ed., Marcel Dekker, New York, pp. 277-316 (1968).
Gersdorff, M.C.H., and Robillard, T.A.J., "'How I do It'—Otology and Neurotology. A Specific Issue and Its Solution. A New Procedure for Bone Reconstruction in Oto-Microsurgery: A Mixture of Bone Dust and Fibrinoagen Adhesive," *Laryngoscope* 95:1278-1280, The Laryngoscope Company (1985).
Gibble, J.W., and Ness, P.M., "Fibrin glue: the perfect operative sealant?," *Transfusion* 30:741-747, American Association of Blood Banks (1990).
Glynn, J.H., and Richardson, J.H., "The Antigenic Properties of Fibrin Films and Foams Prepared from Human and from Bovine Blood Plasma," *J. Immunol.* 53:143-150, The Williams & Wilkins Company (1946).
Gospodarowicz, D., et al., "Structural Characterization and Biological Functions of Fibroblast Growth Factor," *Endocr. Rev.* 8:95-114, The Endocrine Society (1987).
Goudarzi, Y.M., "Clinical Experiences with a Fibrin-Nebacetin Bone Marrow Combination in the Treatment of Chronic Bone Infections and as Local Infection Prophylaxis in Non-Infected Bone Diseases," *Akt. Traumatol.* 13:205-209, Georg Thieme Verlag Stuttgart (1983).
Graham, L.M., et al., "Expanded polytetrafluoroethylene vascular prostheses seeded with enzymatically derived and cultured canine endothelial cells," *Surgery* 91:550-559, The C.V. Mosby Co. (1982).
Greco, F., et al., "Fibrin-antibiotic mixtures: An in vitro study assessing the possibility of using a biologic carrier for local drug delivery," *J. Biomed. Mater, Res.* 25:39-51, John Wiley & Sons, Inc. (1991).
Greenhalgh, D.G., et al., "PDGF and FGF Stimulate Wound Healing in the Genetically Diabetic Mouse," *Am. J. Path.* 136:1235-1246, American Association of Pathologists (1990).
Greisler, H.P., et al., "Endothelial Cell Growth Factor Attachment to Biomaterials," *Trans. Am. Soc. Artif. Intern. Organs* 32:346-349, American Society for Artificial Internal Organs (1986).
Greisler, H.P., et al., "Biomaterial pretreatment with ECGF to augment endothelial cell proliferation," *J. Vasc. Surg.* 5:393-399 and 402, Mosby-Year Book, Inc. (1987).
Greisler, H.P., et al., "Enhanced endothelialization of expanded polytetrafluoroethylene grafts by fibroblast growth factor type 1 pretreatment," *Surgery* 112:244-255, Mosby-Year Book, Inc. (1992).

(56) References Cited

OTHER PUBLICATIONS

Greisler, H.P., et al., "Enhancement of Polytetrafluoroethylene Endothelialization by Pretreatment with Fibrin Glue Containing Heparin Binding Growth Factor-Type I (HBGF-1)," presented at the *Proceedings of the Cardiovascular Science and Technology Conference*, p. 50 (Dec. 2-4, 1991).
Gundry, S.R., and Behrendt, D.M., "A Quantitative and Qualitative Comparison of Fibrin Glue, Albumin, and Blood as Agents to Pretreat Porous Vascular Grafts," *J. Surg. Res. 43*:75-77, Academic Press, Inc. (1987).
Harker, L.A., et al., "Platelet Consumption by Arterial Prostheses: The Effects of Edothelialization and Pharmacologic Inhibition of Platelet Function," *Ann. Surg. 186*:594-601, Lippincott Williams & Wilkins (1977).
Harris, H.I., "Heterogenous Skin Grafts by Coagulum Contact Method," *Am. J. Surg, 65*:315-320, The American Journal of Surgery, Inc. (1944).
Harrison, J.H., and Trichel, B. E., "Experiences with Fibrin Coagulum in Pyelolithotomy," *J. Urol. 62*:1-12, The Williams & Wilkins Company (1949).
Harrison, E.T. et al., "Osteogenin Promotes Reexpression of Cartilage Phenotype by Dedifferentiated Articular Chondrocytes in Serum-Free Medium," *Exp. Cell Res. 192*:340-345, Academic Press, Inc, (1991).
Härting, F., et al., "Glued Fixation of Split-Skin Graft to the Bony Orbit Following Exenteration," *Plas. Reconstruc. Surg. 76*:633-635, Lippincott Williams & Wilkins (1985).
Hattori, T., "Experimental Investigations of Osteogenesis and Chondrogenesis by Implant of BMP-Fibrin Glue Mixture," *J. Jpn. Orthop. Assoc. 64*:824-834, Japanese Orthopedic Association (1990).
Haverich, A., et al., "The Use of Fibrin Glue for Sealing Vascular Prostheses of High Porosity," *Thorac. Cardiovasc. Surgeon 29*:252-254, Georg Thieme Verlag Stuttgart (1981).
Haverich, A., et al., "Evaluation of Fibrin Seal in Animal Experiments," *Thorac. Cardiovasc. Surgeon 30*:215-222, Georg Thieme Verlag Stuttgart (1982).
Haverich, A., et al., "Histopathological Evaluation of Woven and Knitted Dacron Grafts for Right Ventricular Conduits: A Comparative Experimental Study," *Ann. Thorac. Surg. 37*:404-411, Elsevier Science Inc. (1984).
Haverich, A., et al.,"Pericardial Flap-Plasty for Protection of the Tracheal Anastomosis in Heart-Lung Transplantation," *J. Card. Surg. 4*:136-139, Future Publishing Company, Inc (1989).
Haverich, A., et al., "Prevention of graft infection by bonding of gentamycin to Dacron prostheses," *J. Vasc. Surg. 15*:187-193, Mosby-Year Book, Inc. (1992).
Hawn, C.v.Z., et al., "Chemical, Clinical, and Immunological Studies on the Products of Human Plasma Fractionation. XIX. A Note on the Use of Fibrinogen and Thrombin in the Surface Treatment of Burns," *J. Clin. Invest. 23*:580-585, The American Society for Clinical Investigation (1944).
Hayek, A., et al., "An In Vivo Model for Study of the Angiogenic Effects of Basic Fibroblast Growth Factor," *Biochem. Biophys. Res. Commun. 147*:876-880, Academic Press, Inc. (1987).
Herring, M.B., et al., "Endothelial Seeding of Polytetrafluoroethylene Popliteal bypasses," *J. Vasc. Surg. 6*:114-118, Mosby-Year Book, Inc. (1987).
Ho, H.-O., et al., "Drug Release From Glutaraldehyde-Treated Fibrin Gels," *Drug Des. Del. 7*:65-73, Harwood Academic Publishers GmbH (1990).
Hoffman, H.A., "Coagulum Pyelolithotomy," *Am. J. Surg. 79*:598-602, Excerpta Medica, Inc. (1950).
Holcomb, J,B., et al., "Implications of New Dry Fibrin Sealant Technology for Trauma Surgery," *Surg. Clin. North Am. 77*:943-952, W.B. Saunders Company (1997).
Ikossi-O'Connor, M.G., et al., "The Role of Fibrin Adhesive in Vascular Surgery," *J. Surg. Oncol. 23*:151-152, Alan R. Liss, Inc. (1983).
Ingraham, F.D., and Bailey, O.T., "Clinical Use of Products of Human Plasma Fractionation. III. The Use of Products of Fibrinogen and Thrombin in Surgery," *J.A.M.A. 126*:680-685, The American Medical Association (1944).
Ingraham, F.D., and Bailey, O.T., "The Use of Products Prepared from Human Fibrinogen and Human Thrombin in Neurosurgery. Fibrin Foams as Hemostatic Agents; Fibrin Films in Repair of Dural Defects and in Prevention of Meningocerebral Adhesions," *J. Neurosurg. 1*:23-39, Charles C. Thomas (1944).
Ingraham, F.D., et al., "Studies on Fibrin Foam as a Hemostatic Agent in Neurosurgery, with Special Reference to its Comparison with Muscle," *J. Neurosurg. 1*:171-181. Charles C. Thomas (1944).
Ingraham, F.D., et al., "The Use of Fibrin Film as Dural Substitute and in the Prevention of Meningocerebral Adhesions. Further Studies and Clinical Results," *J.A.M.A. 128*:1088-1091, The American Medical Association (1945).
International Search Report for International Application No. PCT/US99/10952, mailed Sep. 17, 1999.
István, L., et al., "Gastrointestinalis vérzések csillapitása thrombin-fibrin készitménnyel," *Orv. Hetil. 105*:219-223, Markusovszky Lajos Foundation (1964).
Jarrell, B., et al., "Human adult endothelial cell growth in culture," *J. Vasc. Surg. 1*:757-764, Mosby-Year Book, Inc. (1984).
Jonas, R.A., et al., "Biological Sealants and Knitted Dacron: Porosity and Histological Comparisons of Vascular Graft Materials with and without Collagen and Fibrin Glue Pretreatments," *Ann. Thorac. Surg. 41*:657-663, Elsevier Science Inc. (1986).
Jonas, R.A., et al., "Biological Sealants and Knitted Dacron Conduits: Comparison of Collagen and Fibrin Glue Pretreatments in Circulatory Models," *Ann. Thorac. Surg. 44*:283-290, Elsevier Science Inc. (1987).
Kabuto, M., et al., "Experimental Study of Intraoperative Local Chemotherapy with Fibrin Glue Containing Nitrosourea for Malignant Gliomas," *Surg. Neurol. 44*:151-157, Elsevier Science Inc. (1995).
Kaehler, J., et al.,"Precoating substrate and surface configuration determine adherence and spreading of seeded endothelial cells on polytetrafluoroethylene grafts," *J. Vasc. Surg. 9*:535-541, The Society for Vascular Surgery and International Society for Cardiovascular Surgery, North American Chapter (1989).
Karck, M., et al., "Pretreatment of prosthetic valve sewing-ring with the antibiotic/fibrin sealant compound as a prophylactic tool against prosthetic valve endocarditis," *Eur. J. Cardio-thorac. Surg. 4*:142-146, Springer-Verlag (1990).
Kawamura, M., and Urist, M.R., "Human Fibrin Is a Physiologic Delivery System for Bone Morphogenetic Protein," *Clin. Orthop. 235*:302-310, Lippincott Williams & Wilkins (1988).
Kempczinski, R.F., et al., "Endothelial cell seeding of a new PTFE vascular prosthesis," *J. Vasc. Surg. 2*:424-429. Mosby-Year Book Inc. (1985).
Kesler, K.A., et al., "Enhanced strength of edothelial attachment on polyester elastomer and polytetrafluorotheylene graft surfaces with fibronectin substrate," *J. Vasc. Surg. 3*:58-64, Mosby-Year Book Inc. (1986).
Knighton, D.R., et al., "Classification and Treatment of Chronic Nonhealing Wounds," *Ann. Surg. 204*:322-330, Lippincott Williams & Wilkins (1986).
Knighton, D.R., et al., "The Use of Platelet Derived Wound Healing Formula in Human Clinical Trials," in *Growth Factors and Other Aspects of Wound Healing: Biological and Clinical Implications*, Alan R. Liss, Inc., pp. 319-329 (1988).
Knighton, D.R., et al., "Regulations of Cutaneous Wound Healing by Growth Factors," *Clin. Mater. 8*:229-241, Elsevier Science Publishers Ltd. (1991).
Knöbl, P.N., et al., "The protein C system in patients undergoing cardiopulmonary bypass," *J. Thorac. Cardiovasc. Surg. 94*:600-605, American Association for Thoracic Surgery (1987).
Kovács, B., and Kerényi, G., "Bioplast® fibrin coagulum in large cystic defects of the jaw," *Intl. J. Oral Surg. 5*:111-116, Elsevier Science Inc. (1976).
Köveker, G., "Clinical Application of Fibrin Glue in Cardiovascular Surgery," *Thorac. Cardiovasc. Surgeon 30*:228-229, Georg Thieme Verlag Stuttgart (1982).

(56) References Cited

OTHER PUBLICATIONS

Köveker, G., et al., "Clinical Experience with Fibrin Glue in Cardiac Surgery," *Thorac. Cardiovasc. Surgeon 29*:287-289, Georg Thieme Verlag Stuttgart (1981).

Köveker, G.B., et al., "Reduction of Thrombogenicity in Small-diameter Vascular Prostheses Seeded with Autologous Endothelial Cells," *Thorac. cardiovasc. Surgeon 34*:49-51, Georg Thieme Verlag Stuttgart (1986).

Kram, H.B, et al., "Use of concentrated fibrinogen in experimental tracheal repair," *J. Biomed. Mater. Res. 20*:579-587, John Wiley & Sons, Inc. (1986).

Kram, H.B., et al., "Fibrin glue sealing of polytetrafluoroethylene vascular graft anastomoses: Comparison with oxidized cellulose," *J. Vasc. Surg. 8*:563-568, Mosby-Year Book, Inc. (1988).

Kram, H.B., et al., "Antibacterial Effects of Fibrin Glue-Antibiotic Mixtures," *J. Surg. Res. 50*:175-178, Academic Press, Inc. (1991).

Kratzat, R., et al., "Klinische Erfahrungen mit dem Fibrin-Antibiotikum-Verbund bei Knochen-und Weichteilinfektionen," *Akt. Chir. 17*:58-62, Georg Thieme Verlag Stuttgart (1982).

Kratzat, R., et al., "Erste klinische Erfarungen mit dem Fibrin-Antibiotikum-Verbund bei der Osteomyelitis," *Orthop. Praxis 17*:852-855, Georg Thieme Verlag Stuttgart (1981).

Kratzat, R., et al., "Klinische Erfahrungen mit dem Fibrin-Antibiotikum-Verbund bei Knochen-und Weichteilinfektionen," in *Fibrinkleber in Orthopadie und Traumatologie*, Cotta et al., eds., Georg Thieme Verlag, Stuttgart, pp. 200-204 (1982).

Kreider, J.W., et al., "Concordance of Condylomata Acuminata Responses to Treatment with Intralesional MPI 5003 and Papiloma Responses in the Shope Rabbit Papilloma Model System," *Skin Pharmacol. 5*:201-202, Karger AG, Basel (1992).

Ksander, G.A., et al., "The effect of platelet releasate on wound healing in animal models," *J. Am. Acad. Dermatol. 22*:781-791, Amedo Group (1990).

Larson, M.J., et al.. "Efficacy of a Fibrin Hemostatic Bandage in Controlling Hemorrhage From Experimental Arterial Injuries," *Arch. Surg, 130*:420-422, American Medical Association (1995).

Lasa, C., et al., "Osteoregeneration Using a Fibrin Sealant Delivery Vehicle for Demineralized Bone Matrix," *J. Cell. Biochem. Suppl. 17E*:162, Abstract No. RZ 217 (Mar. 29-Apr. 4, 1993).

Lasa, C.I., et al., "Effect of Fibrin Glue and Opsite on Open Wounds in DB/DB Mice," *J. Surg. Res. 54*:202-206, Academic Press, Inc. (1993).

Lerner, R., and Binur N.S., "Current Research Review. Current Status of Surgical Adhesives," *J. Surg. Res. 48*:165-181, Academic Press, Inc. (1990).

Lindner, V., et al., "Basic Fibroblast Growth Factor Stimulates Endothelial Regrowth and Proliferation in Denuded Arteries," *J. Clin. Invest. 85*:2004-2008, The American Society for Clinical Investigation, Inc. (1990).

Lobb, R.R., "Clinical applications of heparin-binding growth factors," *Eur. J. Clin. Invest. 18*:321-336, 39 Blackwell Science Ltd. (1988).

Lucht, U., et al., "Fibrin sealant in bone transplantation," *Acta. Orthop. Scand. 57*:19-24, Scandinavian University Press (1986).

Luyten, F.P., et al., "Purification and Partial Amino Acid Sequence of Osteogenin, a Protein Initiating Bone Differentiation," *J. Biol. Chem. 264*: 13377-13380, American Society of Biochemistry and Molecular Biology Inc. (1989).

Lynch, S.E., et al., "Growth Factors in Wound Healing," *J. Clin. Invest. 84*:640-646, The American Society for Clinical Investigation, Inc. (1989).

MacPhee, M., et al., "Fibrin Sealant Based Bandages and Foam: Hemostatic Devices for Treatmetn of Combat Casualties on the Battlefield," presented at the *Advanced Technology Applications to Combat Casualty Care (ATACCC) Conference* (May 17-18, 1995).

MacPhee, M., "Field-Ready Fibrin Sealant Based Hemostatic Devices," presented at the *29th Penner Blood Conference* (May 1995).

MacPhee, M., et al., "Fibrin Sealant Based Hemostatic Devices for Treatment of Trauma in the Field," presented at the *FDA-Army Conference on Fibrin Sealant* (Dec. 1994).

Mark, D.E., et al., "Repair of Calvarial Nonunions by Osteogenin, a Bone-Inductive Protein," *Plast. Reconstr. Surg. 86*:623-630, Lippincott Williams & Wilkins (1990).

Massagué, J., "The TGF-β Family of Growth and Differentiation Factors," *Cell 49*:437-438, Cell Press (1987).

Matras, H., "Fibrin Seal: The State of the Art," *J. Oral Maxillofac. Surg. 43*:605-611, W.B. Saunders Co. (1985).

McEvitt, W.G., "Experiences with Fibrin Fixation Methods of Skin Grafting. A Clinical Evaluation," *J. Mich. State Med. Assoc. 44*:1347-1351, Michigan State Medical Society (1945).

McGee, G.S., et al., "Recombinant Basic Fibroblast Growth Factor Accelerates Wound Healing," *J. Surg. Res. 45*:145-153, Academic Press, Inc. (1988).

Michael, P., and Abbot, W., "The Use of Human Fibrinogen in Reconstructive Surgery," *J.A.M.A. 123*:279, The American Medical Association (1943).

Miller, B.H., et al., "Basal cell carcinomas histologically resolved after treatment with intralesional 5-Fluorouracil Therapeutic Implant," *Proc. Amer. Assoc. Cancer Res. 32*:420 Abstract No. 2496, The American Association for Cancer Research (1991).

Montesano, R., et al., "Basic fibroblast growth factor induces angiogenesis in vitro," *Proc. Natl. Acad. Sci. USA 83*:7297-7301, The National Academy of Sciences (1986).

Moore, T,D., and Sweetser, Jr., T.H., "Coagulum Pelviolithotomy; an Improved Technique," *J Urol. 67*:579-584, The Williams & Wilkins Company (1952).

Moore, W.S., et al., "Development of an Infection-Resistant Vascular Prosthesis," *Arch. Surg. 116*:1403-1407, American Medical Association (1981).

Morrison, P.R., and Singer, M., "Chemical, Clinical, and Immunological Studies on the Products of Human Plasma Fractionation. XVII. A Note on the Absorption Rates of Fibrin Films in Tissue," *J. Clin. Invest. 23*:573-575, The American Society for Clinical Investigation (1944).

Mustoe, T.A., et al., "Accelerated Healing of Incisional Wounds in Rats Induced by Transforming Growth Factor-β," *Science 237*:1333-1336, American Asociation for the Advancement of Science (1987).

Nowotny, R., et al., "Mechanical Properties of Fibrinogen-Adhesive Material," *Biomaterials 3*:677-682, John Wiley and Sons Ltd. (1982).

Orenberg, E.K., et al., "The effect of intralesional 5-Fluorouracil Therapeutic Implant (MPI 5003) for treatment of basal cell carcinoma," *J. Am. Acad. Dermatol. 27*:723-728, American Academy of Dermatology (1992).

Petrelli, N.J., et al., "The Application of Tissue Adhesives in Small Bowel Anastomoses," *J. Surg. Oncol. 19*:59-61, Alan R. Liss, Inc. (1982).

Pierce, G.F., et al., "In Vivo Incisional Wound Healing Augmented by Platelet-Derived Growth Factor and Recombinant c-sis Gene Homodimeric Proteins," *J. Exp. Med. 167*:974-987, The Rockefeller University Press (1988).

Pop, M., et al., "Experimental covering of the dental pulp in the dog with biological substances," Chemical Abstracts 72:209 Abstract No. 119944n, The American Chemical Society (1970).

Presta, M., et al., "Basic fibroblast growth factor requires a long-lasting activation of protein kinase C to induce cell proliferation in transformed fetal bovine aortic endothelial cells," *Cell Regul. 2*:719-726, The American Society for Cell Biology (1991).

Puumala, M., et al., "Intraventricular infusion of HBGF-2 promotes cerebral angiogenesis in Wistar Rat," *Brain Res. 534*:283-286, Elsevier Science Publishers B.V. (1990).

Radomski, J.S., et al., "Initial Adherence of Human Capillary Endothelial Cells to Dacron," *J. Surgical Res. 42*:133-140, Academic Press, Inc. (1987).

Ramalanjaona, G., et al., "The effect of fibronectin coating on endothelial cell kinetics in polytetrafluorcethylene grafts," *J. Vasc. Surg. 3*:264-272, Mosby-Year Book Inc. (1986).

Redl H., et al., "Fibrinkleber-Antibiotika-Gernische—Festigkeit und Elutionsverhalten," in *Fibrinkleber in Orthopadie und Traurnatologie*, Cotta et al., eds., Georg Thieme Verlag, Stuttgart, pp. 178-181 (1982).

(56) References Cited

OTHER PUBLICATIONS

Redl, H., et al., "In vitro properties of mixtures of fibrin seal and antibiotics," *Biomaterials* 4:29-32, Butterworth & Co. (1983).
Roberts, A.B., and Sporn, M.B., "Transforming Growth Factor β," *Adv. Cancer Res.* 51:107-145, Academic Press Inc. (1988).
Rothe, M., and Falanga, V., "Growth Factors. Their Biology and Promise in Dermatologic Diseases and Tissue Repair," *Arch. Dermatol.* 125:1390-1398, American Medical Association (1989).
Rovee, D.T., "Evolution of Wound Dressings and their Effects on the Healing Process," *Clin. Mater.* 8:183-188, Elsevier Science Publishers Ltd. (1991).
Sakurai, T., et al., "Controlled release of sisomicin from fibrin glue," *J. Control. Release* 18:39-44, Elsevier Science Publishers B.V. (1992).
Sauvage, L.R., et al., "Interspecies Healing of Porous Arterial Prostheses. Observations, 1960 to 1974," *Arch. Surg.* 109:698-705, American Medical Association (1974).
Schlag, G., and Redl, H.G., "Fibrin Sealant in Orthopedic Surgery," *Clin. Orthop.* 227:269-285, Lippincott Williams & Wilkins (1988)
Schrenk, P., et al., "Fibrin Glue Coating of e-PTFE Prostheses Enhances Seeding of Human Endothelial Cells," *Thorac. Cardiovasc. Surgeon* 35:6-10, Georg Thieme Verlag Stuttgart (1987).
Schultz, G.S., et al., "Epithelial Wound Healing Enhanced by Transforming Growth Factor-α and Vaccinia Growth Factor," *Science* 235:350-352, American Association for the Advancement of Science (1987).
Schwarz, N., et al., "The Influence of Fibrin Sealant on Dermineralized Bone Matrix-Dependent Osteoinduction," *Clin. Orthop.* 238:282-287, Lippincott Williams & Wilkins (1989).
Senderoff, R.L., et al., "Fibrin Based Drug Delivery Systems," *J. Parenteral Sci. Tech.* 45:2-6, Parenteral Drug Association (1991).
Sheehan, J.E., "Plasma Fixation of Skin Grafts," *Am. J. Surg.* 65:74-78, The American Journal of Surgery, Inc. (1944).
Shindo, S., et al., "Improved patency of collagen-impregnated grafts after in vitro autogenous endothelial cell seeding," *J. Vasc. Surg.* 6:325-332, Mosby-Year Book, Inc (1987).
Shoemaker, S.C., et al., "Effects of fibrin sealant on incorporation of autograft and xenograft tendons within bone tunnels," *Am. J. Sports Med.* 17:316-324, American Orthopaedic Society for Sports Medicine (1989).
Silbermann, M., "In vitro systems for inducers of cartilage and bone development," *Biomaterials* 11:47-49, Butterworth-Heinemann Ltd. (1990).
Silberstein, L.E. et al., "An autologous fibrinogen-based adhesive for use in otologic surgery," *Transfusion* 28:319-321, American Association of Blood Banks (1988).
Spotnitz, W.D., et al., "Fibrin Glue from Stored Human Plasma. An Inexpensive and Efficient Method for Local Blood Bank Preparation," *Am. Surg.* 53:460-462, Southeastern Surgical Congress (1987).
Sprugel, K.H., et al., "The Effects of Different Growth Factors in Subcutaneous Wound Chambers," in *Growth Factors and Other Aspects of Wound Healing: Biological and Clinical Implications*, Barbul, A., et al., eds., Alan R.Liss, Inc., New York, NY, pp. 77-91 (1988).
Stark, J., and de Leval, M., "Experience with Fibrin Seal (Tisseel) in Operations for Congenital Heart Defects," *Ann. Thorac. Surg.* 38:411-413, Elsevier Science Inc, (1984).
Stemberger, A., and Blümel, G., "Fibrinogen-Fibrin Conversion and Inhibition of Fibrinolysis," *Thorac. Cardiovasc. Surgeon* 30:209-214, Georg Thieme Verlag Stuttgart (1982).
Stoll, H.-G., "Koagulum-Pyelolithotomie," *Zeitschrift für Urologie* 52:610-615, Georg Thieme Leipzig (1959).
Sugie, I., et al., "The chemical modification of fibrin film as artificial skin," *Chemical Abstracts* 85:318, The American Chemical Society, Abstract No. 182381k (1976).
Sugitachi, A., et al., "A Newly Designed Anticancer Tumor Immunity Drug Delivery System," *Trans. Am. Soc. Artif. Intern. Organs* 37:M177-M178, American Society for Artificial Internal Organs (1991).

The American Red Cross, "Growth Factor-Supplemented Fibrin Glue," in *The American Red Cross Biomedical Research and Development Report*, p. 20, The American Red Cross (1990).
The American Red Cross, "Growth Factor-Supplemented Fibrin Glue," in *The American Red Cross Biomedical Research and Development Report*, p. 21, The American Red Cross (1989).
Thompson, D.F., et al., "Fibrin Glue: A Review of Its Preparation, Efficacy, and Adverse Effects as a Topical Hemostat," *Drug Intell. Clin. Pharm.* 22:946-952, Cincinnati OH Drug Intelligence (1988).
Thompson, J.A.. et al., "Site-Directed Neovessel Formation in Vivo," *Science* 241:1349-1352, American Association for the Advancement of Science (1988).
Thompson, J.A., et al., "Heparin-binding growth factor 1 induces the formation of organoid neovascular structures in vivo," *Proc. Natl. Acad. Sci. USA* 86:7928-7932, The National Academy of Sciences (1989).
Thorson, G.K., et al., "The Role of the Tissue Adhesive Fibrin Seal (FS) in Esophageal Anastomoses," *J. Surg. Oncol.* 24:221-223, Alan R. Liss, Inc. (1983).
Tidrick, R.T., and Warner, E.D., "Fibrin Fixation of Skin Transplants," *Surgery* 15:90-95, The C.V. Mosby Company (1944).
Tsuboi, R., and Rifkin, D.B., "Recombinant Basic Fibroblast Growth Factor Stimulates Wound Healing in Healing-impaired db/db Mice," *J. Exp. Med.* 172:245-251, The Rockefeller University Press (1990).
Ulatowski, L., et al., "Neue Aspekte der Anwendung eines erweiterten Fibrinklebesystems (FKS)," *Orthop. Praxis* 15:795-799, Kluwer Academic (1979).
Ulatowski, L., et al., "Zur Wirkung eines Fibrin-Antibiotikum-Verbundes bei Knochen- und Weichteil-Infektionen," *Fortschr. Med.* 99:864-868, Krause& Pachernegg GmbH (1981).
Ulatowski, L., et al., "Pharmakokinetik eines Fibrinantibiotikumverbundes," in *Fibrinkleber in Orthopadie und Traumatologie*, Cotta et al., eds., Georg Thieme Verlag, Stuttgart, pp. 196-199 (1982).
Urist, M.R., and Strates, B.S., "Bone Formation in Implants of Partially and Wholly Demineralized Bone Matrix," *Clin. Orthop.* 71:271-278, Lippincott Williams & Wilkins (1970).
Urist, M.R., et al., "Bone Morphogenesis in Implants of Insoluble Bone Gelatin," *Proc. Natl. Acad. Sci. USA* 70:3511-3515, The National Academy of Sciences (1973).
Walterbusch, G., et al., "Clinical Experience with Fibrin Glue for Local Bleeding Control and Sealing of Vascular Prostheses," *Thorac. Cardiovasc. Surgeon* 30:234-235, Georg Thieme Verlag Stuttgart (1982).
Wang, E.A., et al., "Bone Morphogenetic Proteins and Bone Repair," *J. Cell Biochem.* Suppl. 0(15 Part F):161, Kluwer Academic (1991).
Watkins, M.T., et al., "Adult Human Saphenous Vein Endothelial Cells: Assessment of Their Reproductive Capacity for Use in Endothelial Seeding of Vascular Prostheses," *J. Surg. Res.* 36:588-596, Academic Press, Inc. (1984).
Weiner, L., and Wald, A.H., "Fibrin Foam and Thrombin as Used in the Surgical Removal of a Large Fibromyxoma of the Mandible," *J. Am. Dent. Assoc.* 33:731-735, American Dental Association (1946).
Weisman, R.A. et al., "Biochemical Characterization of Autologous Fibrinogen Adhesive," *Laryngoscope* 97:1186-1190, Lippincott Williams & Wilkins (1987).
Williams, S.K., et al., "Adult Human Endothelial Cell Compatibility with Prosthetic Graft Material," *J. Surgical Res.* 38:618-629, Academic Press, Inc, (1985).
Winter, L., et al., "Experimentelle and klinische Anwendung der aus Rinderplasma hergestellten Fibrinprodukte. III. Klinische Verwendung von hämostatischen Fibrinprodukten," *Zentralblatt für Chirurgie* 78:469-479, Vereinigung Mitteirheinischer Chirurgen (1953).
Woodhall, B., "Fibrin Foam as a Hemostatic Agent in Rehabilitation Neurosurgery," *J.A.M.A.* 126:469-471, The American Medical Association (1944).
Yu, N., et al., "Comparison of Antitumor Effects of Treatment Sequence of Fluorouracil (FU) and Cisplatin (Pt) Therapeutic Implants in a Mouse Tumor Model," *Proc. Annu. Meet. Am. Soc. Clin. Oncol.* 11:100, American Society of Clinical Oncology, Abstract No. 223 (1992).

(56) References Cited

OTHER PUBLICATIONS

Yu, N., et al., "Pharmacokinetics and Clinical Application of the Intralesional Methotrexate Therapeutic Implant," *Proc. Annu. Meet. Am. Soc. Clin. Oncol. 11*:100, American Society of Clinical Oncology, Abstract No. 222 (1992).

Zilla, P., et al., "Use of fibrin glue as a substrate for invitro endothelialization of PTFE vascular grafts," *Surgery 105*:515-522, Mosby-year Book Inc. (1989).

Zilch, H., et al., "Diffusionsverhalten von Cefotaxim aus der Fibrin-Antibiotika-Plombe im Tierversuch," in Fibrinkleber in Orthopadie und Traumatologie, Cotta et al., eds., Georg Thieme Verlag, Stuttgart, pp. 191-195 (1982).

Zilch, H., and Lambris, E., "The Sustained Release of Cefotaxim from a Fibrin-Cefotaxim Compound in Treatment of Osteitis," *Arch. Orthop. Trauma Surg. 106*:36-41, Springer-Verlag (1986).

Dialog® File No. 351, Accession No, 2271477, Dewent WPI English language abstract of JP 54-104687, Aug. 17, 1979.

Dialog® File No. 351, Accession No. 3493656, Derwent WPI English language abstract of DE 3,037,270, May 19, 1982.

Dialog® File No. 351, Accession No. 4485878, Derwent WPI English language abstract of JP 60-204725, Oct. 16, 1985.

Dialog® File 351, Accession No. 3793917, Derwent WPI English language abstract of EP 0 090 997 A2, Oct. 12, 1983.

English translation of JP 62-246370, translated by Translation Services PTY Ltd, translation dated Mar. 6, 2001.

English translation of JP 63-115564, translated by Translation Services PTY Ltd, translation dated Mar. 13, 2001.

English translation of the first full paragraph on p. 28 of Afra, D., et al., "Experimentelle Untersuchung der Resorption von Fibrinfilmen und ihre Anwendung in der neurochirurgischen Praxis", *Acta. Med. Acad. Sci. Hung. 11*:1-29, Hungarian Academy of Sciences (1958), translated by McElroy Translation Company (dated Aug. 24, 2001).

English translation of the second-fifth paragraphs on p. 852 of Bagdy. D., et al., "Experimentelle und klinische Anwendung der aus Rinderplasma hergesteliten Fibrinprodukte," *Zentralblatt für Chirurgie 77*:848-852, Vereinigung Mitteirheinischer Chirurgen (1952), translated by McElroy Translation Company (dated Aug. 24, 2001).

English translation of the fourth-sixth paragraphs on p. 152 and the sixth paragraph on p. 184 of Bagdy D., et al., *in Trombin-Fibrinprodukte und Ihre Therapeutische Anwendung*, pp. 152-159, 184-187, Veb Gustav Fischer Verlag Jena (1963), translated by McElroy Translation Company (dated Aug. 24, 2001).

English translation of the first full column at p. 219 of István, L., et al., "Gastrointestinalis vérzések csillapitása thrombin-fibrin készilménnyel," *Orv. Hetil. 105*:219-223, Markusovszky Lajos Foundation (1964), translated by McElroy Translation Company (dated Aug. 24, 2001).

English translation of the third-fourth paragraphs on p. 615 of Stoll, H.G., "Koagulum-Pyelolithotomie," *Zeitschtift für Urologie 52*:610-615, Veb Georg Thieme Leipzig (1959), translated by McElroy Translation Company (Aug. 24, 2001).

Berguer, R., et al., "Warning: Fatal Reaction to the Use of Fibrin Glue in Deep Hepatic Wounds. Case Reports," *J. Trauma 31*:408-411, Williams & Wilkens Company (1991).

Cziperle, D., et al., "Enhanced Endothelialization of Expanded Polytetrafluoroethylene Grafts by Heparin Binding Growth Factor-Type 1 (HBGF-1) Pretreatment," presented at the Society of University Surgeons (1992).

de la Garza, J.L. and Rumsey Jr., E., "Fibrin Glue and Hemostasis in Liver Trauma: A Case Report," *J. Trauma 30*:512-513, Williams & Wilkens Company (1990).

Jakob, H., et al., "Use of fibrin sealant for reinforcing arterial anastomoses," *J. Vasc. Surg. 1*:171-180, C.V. Mosby Company (1984).

Kendrick, D.B., et al., "Plasma Fractionation," in *Blood Program in World War II*, Coates, Jr., J.B. and McFetridge, E.M., eds., Office of the Surgeon General, Dept. of the Army, Washington, D.C., pp. 363-369 (1964).

Kram, H.B., et al., "Techniques of Splenic Preservation Using Fibrin Glue," *J. Trauma 30*:97-101, Williams & Wilkens Company (1990).

Ochsner, M.G., et al., "Fibrin Glue as a Hemostatic Agent in Hepatic and Splenic Trauma," *J. Trauma 30*:884-887, Williams & Wilkens Company (1990).

Matthew, T.L., et al., "Four Years' Experience With Fibrin Sealant in Thoracic and Cardiovascular Surgery," *Ann. Thorac. Surg. 50*:40-44, Elsevier (1990).

Ness, P.M., et al., "Cryoprecipitate as a Reliable Source of Fibrinogen Replacement," *JAMA 241*:1690-1691, American Medical Association (1979).

Rapaport, S.I., et al., "Clinical Significance of Antibodies to Bovine and Human Thrombin and Factor V After Surgical Use of Bovine Thrombin," *Am. J. Clin. Pathol. 97*:84-91, J.B. Lippincott Company (1992).

Reiss, R.F. and Oz, M.C., "Autologous Fibrin Glue: Production and Clinical Use," *Transfus. Med. Rev. 10*:85-92, W.B. Saunders Company (1996).

Rocko, J.M. et al., "A.A.S.T. Abstracts: Exsanguination in public—a preventable death," *J. Trauma 22*:635, Williams & Wilkens Company (1982).

Schiele, U., et al., "Haemostyptic Preparations on the Basis of Collagen alone and as fixed Combination with Fibrin Glue," *Clin. Mater. 9*:169-177, Elsevier Science Publishers, Ltd. (1992).

Sloand, E.M., et al., "Safety of the Blood Supply," *JAMA 274*, :1368-1373, American Medical Association (1995).

Spotnitz, W.D., "Fibrin Sealant in the United States: Clinical Use at the University of Virginia," *Thromb. Haemost. 74*:482-485, Stuttgart F.K. Schattauer Verlag (1995).

Zimmerman, L.M., and Veith, I., "Celsus and the Alexandrians," in *Great Ideas in the History of Surgery*, Zimmerman, L.M., and Veith, I., eds., Norman Publishing, San Francisco, CA, p. 31 (1993).

HEMOSTATIC DRESSING

BACKGROUND OF THE INVENTION

1. Field of the Invention

The present invention relates to a hemostatic dressing that comprises a plurality of layers that contain resorbable materials and/or coagulation proteins. The hemostatic dressing is useful for the treatment of wounded tissue.

2. Background of the Invention

The control of hemorrhage (bleeding) is a critical step in first aid and field trauma care. Unfortunately, the occurrence of excessive bleeding or fatal hemorrhage from an accessible site is not uncommon. J. M. Rocko et al, J. Trauma 22:635 (1982). Mortality data from Vietnam indicates that 10% of combat deaths were due to uncontrolled extremity hemorrhage. SAS/STAT Users Guide, 4th ed. (Cary, N.C.: SAS Institute Inc; 1990). Up to one third of the deaths from exsanguination during the Vietnam War could have been prevented by the use of effective field hemorrhage control methods. SAS/STAT Users Guide, 4th ed. (Cary, N.C.: SAS Institute Inc; 1990).

Although civilian trauma mortality statistics do not provide exact numbers for prehospital deaths from extremity hemorrhage, case and anecdotal reports indicate similar occurrences. J. M. Rocko et al., J. Trauma 22:635 (1982). These data suggest that a substantial increase in survival can be effected by the prehospital use of a simple and effective method of hemorrhage control.

Liquid fibrin sealants have been used as an operating room adjunct to hemorrhage control. J. L. Garza et al., J. Trauma 30:512-513 (1990); H. B. Kram et al., J. Trauma 30:91-101 (1990); M. G. Ochsner et al., J. Trauma 50:884-887 (1990); T. L. Matthew et al., Ann. Thorac. Surg. 50:40-44 (1990); H. Jakob et al., J. Vasc. Surg., 1:171-180 (1984). The widespread use of fibrinogen and thrombin was common in the last year of World War $\pi$, but was abandoned because of the transmission of hepatitis. D. B. Kendrick, Blood Program in WW II (Washington, D.C.: Office of the Surgeon General, Department of Army; 1989), 363-368.

Single donor fibrin sealants have been widely used clinically, not only for hemorrhage control but in various surgical situations. W. D. Spotnitz, Thromb. Haemost. 74:482-485 (1995); R. Lerner et al., Surg. Res. 48: 165-181 (1990). The American Red Cross and others have developed plasma protein purification methods that seem to eliminate the hepatitis risk. Reiss et al., Trans. Med. Rev. 70:85-92 (1996).

A dry fibrinogen-thrombin dressing (TACHOCOMB™, Hafslund Nycomed Pharma, Linz, Austria) is also available for operating room use in many European countries. Schiele et al., Clin. Materials 9:169-177 (1992). Present formulations of this dressing use bovine thrombin. While this fibrinogen-thrombin dressing requires no premixing and is easy to use, its utility is limited by a requirement for storage at 4° C. and the necessity for prewetting with saline solution prior to application to the wound.

A hemostatic sandwich dressing has been described, which contains a layer of thrombin sandwiched between layers of fibrinogen (see, e.g., PCT/US99/10952, which is incorporated herein by reference). Although such dressings can be used in methods for treating wounded tissue, such conventional sandwich dressings can become delaminated, whereby the edges of the layers of the dressing no longer adhere to each other. Such delamination can result in reduced interaction of the dressing components layers, with decreased effectiveness of the dressing in preventing hemorrhage.

BRIEF SUMMARY OF THE INVENTION

The present invention provides a hemostatic dressing (e.g., a bandage) that includes a layer of thrombin sandwiched between a first and a second layer of fibrinogen, wherein the thrombin layer is noncoextensive with the first and/or second fibrinogen layer. Such a hemostatic dressing is useful for treating wounds and offers the unexpected advantage of inhibiting delamination of the layers, as compared with dressings in which the thrombin layer is coextensive with the entire first and second fibrinogen layers.

Thus, the present invention provides a hemostatic dressing which comprises: (i) a first fibrinogen layer; (ii) a thrombin layer adjacent to the first fibrinogen layer; and (iii) a second fibrinogen layer adjacent to the thrombin layer, wherein the thrombin layer is non-coextensive with the first and/or second fibrinogen layers of the hemostatic dressing.

A related dressing of the invention comprises: (i) a resorbable material layer, (ii) a first fibrinogen layer adjacent to the resorbable material layer, (iii) a thrombin layer adjacent to the first fibrinogen layer; and (iv) a second fibrinogen layer adjacent to the thrombin layer, wherein the thrombin layer is noncoextensive with the first and/or second fibrinogen layers of the hemostatic dressing In another embodiment, the hemostatic dressing comprises: (i) a first fibrinogen layer, (ii) a resorbable material layer adjacent to the first fibrinogen layer, (iii) a thrombin layer adjacent to the resorbable material layer, and (iv) a second fibrinogen layer adjacent to the thrombin layer, wherein the thrombin layer is non-coextensive with the first and/or second fibrinogen layers of the hemostatic dressing.

The invention also includes methods for treating wounded tissue in a patient, which comprise applying any of the novel hemostatic dressings described herein to wounded tissue. In such methods, the hemostatic dressing can be hydrated with liquids that are exogenous to the wounded tissue, or they can be hydrated with liquids that are endogenous to the wounded tissue.

Also included within the invention are methods for preparing a hemostatic dressing by providing a first layer of fibrinogen, applying a layer of thrombin to the first layer of fibrinogen, and applying a second layer of fibrinogen to the layer of thrombin, wherein the layer of thrombin is noncoextensive with the first fibrinogen layer and/or noncoextensive with the second fibrinogen layer.

Similarly, the invention includes a method for preparing a hemostatic dressing by providing a resorbable or nonresorbable backing layer having attached thereto a first layer of fibrinogen; applying a layer of thrombin to said first layer of fibrinogen on a side of the fibrinogen layer that is opposite of the side to which the resorbable or nonresorbable backing layer is attached; and applying a second layer of fibrinogen to the layer of thrombin, wherein the layer of thrombin is non-coextensive with the first fibrinogen layer and/or noncoextensive with the second fibrinogen layer.

In various embodiments, the thrombin layer is coextensive with 5% to 95% (e.g., 20 to 50%) of the first and second fibrinogen layers, independently. The thrombin layer can be configured in any of a variety of shapes and patterns. For example, and without limitation, the thrombin layer can be configured as an array of spots comprising thrombin, or as a single spot comprising thrombin. Alternatively, the thrombin layer can be configured as a plurality of lines comprising thrombin.

Each layer of the hemostatic dressings can also optionally contain one or more suitable fillers, binding agents and/or solubilizing agents. In addition, each of the hemostatic dressings can also optionally further comprise a release layer which contains a release agent and/or a backing material.

It is to be understood that both the foregoing general description and the following detailed description are exemplary and explanatory only and are intended to provide further explanation of the invention as claimed.

Unless defined otherwise, all technical and scientific terms used herein have the same meaning as is commonly understood by one of skill in the art to which this invention belongs. All patents, patent applications, and publications mentioned herein are incorporated herein by reference.

As used herein, a thrombin layer that is said to be "noncoextensive" with a fibrinogen layer is one in which the spatial boundaries of the thrombin layer in two dimensions are smaller than the spatial boundaries of one or both fibrinogen layers such that the thrombin layer is coextensive with only about 5% to about 95% of the surface area of the first fibrinogen layer of the hemostatic dressing and/or coextensive with only about 5% to about 95% of the surface layer of the second fibrinogen layer of the hemostatic dressing, independently. For example, the thrombin layer can be coextensive with about 10, 20, 30, 40, 50, 60, 70, 75, 80, or 90% of the surface area of each of the first and second fibrinogen layers, independently. A thrombin layer that is "coextensive" with a fibrinogen layer provides full coverage of the fibrinogen layer and is coextensive with 100% of the surface area of the fibrinogen layer. A thrombin layer can be noncoextensive with the first fibrinogen layer and yet be coextensive with the second fibrinogen layer, or vice versa, e.g., by employing fibrinogen layers having different total surface areas or shapes.

"Patient" as used herein refers to human or animal individuals in need of medical care and/or treatment.

"Wound" as used herein refers to any damage to any tissue of a patient that results in the loss of blood from the circulatory system. The tissue can be an internal tissue, such as an organ or blood vessel, or an external tissue, such as the skin. The loss of blood can be internal, such as from a ruptured organ, or external, such as from a laceration. A wound can be in a soft tissue, such as an organ, or in hard tissue, such as bone. The damage may have been caused by any agent or source, including traumatic injury, infection or surgical intervention. The damage can be life-threatening or non-life-threatening.

"Resorbable material" as used herein refers to a material that is broken down spontaneously and/or by the mammalian body into components which are consumed or eliminated in such a manner as not to interfere significantly with wound healing and/or tissue regeneration, and without causing any significant metabolic disturbance.

"Stability" as used herein refers to the retention of those characteristics of a material that determine activity and/or function.

"Binding agent" as used herein refers to a compound or mixture of compounds that improves the adherence of one layer of the hemostatic dressing to one or more different layers and/or the adherence of the components of a given layer to other components of that layer.

"Solubilizing agent" as used herein refers to a compound or mixture of compounds that improves the dissolution of a protein or proteins in aqueous solvent.

"Filler" as used herein refers to a compound or mixture of compounds that provide bulk and/or porosity to one or more layers of the hemostatic dressings.

"Release agent" as used herein refers to a compound or mixture of compounds that facilitates removal of an hemostatic dressing from a manufacturing mold.

"Foaming agent" as used herein refers to a compound or mixture of compounds that produces gas when hydrated under suitable conditions.

As used herein, "about" means plus or minus approximately ten percent of the indicated value.

The hemostatic dressing of the invention offers various advantages as compared with conventional dressings. By using a thrombin layer that is noncoextensive with one or both fibrinogen layers, the dressings of the invention are less likely to become delaminated at their edges, thus rendering the dressings more durable and easier to handle than conventional dressings. In addition, such dressings are more amenable to large-scale manufacturing and provide for better control of the amount of thrombin dispensed in the dressing.

Other features and advantages of the invention will be apparent from the following detailed description, and from the claims.

DETAILED DESCRIPTION OF THE INVENTION

An exemplary embodiment of the present invention is directed to a hemostatic dressing, e.g., for treating wounded tissue in a patient, which comprises: (i) a first fibrinogen layer; (ii) a thrombin layer adjacent to the first fibrinogen layer; and (iii) a second fibrinogen layer adjacent to the thrombin layer, wherein the thrombin layer is noncoextensive with the first and/or second fibrinogen layers.

Another embodiment of the present invention is directed to a hemostatic dressing which comprises: (i) a resorbable material layer; (ii) a first fibrinogen layer adjacent to the resorbable material layer; (iii) a thrombin layer adjacent to the first fibrinogen layer; and (iv) a second fibrinogen layer adjacent to the thrombin layer, wherein the thrombin layer is noncoextensive with the first and/or second fibrinogen layers.

Yet another embodiment of the present invention is directed to a hemostatic dressing for treating wounded tissue in a patient which comprises: (i) a first fibrinogen layer; (ii) a resorbable material layer adjacent to the first fibrinogen layer; (iii) a thrombin layer adjacent to the resorbable material layer; and (iv) a second fibrinogen layer adjacent to the thrombin layer, wherein the thrombin layer is noncoextensive with the first and/or second fibrinogen layers.

Each layer of the hemostatic dressings can also optionally contain one or more suitable fillers, such as sucrose.

Each layer of the hemostatic dressings can also optionally contain one or more suitable binding agents, such as sucrose.

Each layer of the hemostatic dressings can also optionally contain one or more suitable solubilizing agents, such as sucrose.

Each layer of the hemostatic dressings can also optionally contain one or more suitable foaming agents, such as a mixture of citric acid and sodium bicarbonate.

Each of the hemostatic dressings can also optionally further comprise a release layer which contains a release agent. An exemplary release agent is sucrose.

Each of the hemostatic dressings can also further comprise a backing material on the side of the dressing opposite the wound-facing side when the dressing is in use. The backing material can be affixed with a physiologically-acceptable adhesive or can be self-adhering (e.g. by having a surface static charge). The backing material can be a resorbable material or a non-resorbable material, such as a silicone patch or plastic.

The fibrinogen employed in the hemostatic dressing can be a fibrinogen complex or any fibrinogen, or a derivative or metabolite thereof (such as fibrinopeptide A and fibrinopeptide B) can be employed as desired. The fibrinogen can also contain Factor XIII.

The fibrinogen complex can be a mixture of human plasma proteins which has been purified and virally inactivated. An exemplary aqueous solution of fibrinogen complex contains 100-130 mg/mL total protein, of which at least 80% is fibrinogen. Other constituents of the fibrinogen complex can include albumin (generally about 5-25 mg mL); plasminogen (generally less than about 5 µg/mL); Factor XIII (generally about 10-40 Units/mL); and polysorbate 80 (generally less than 3%). The pH of the fibrinogen complex is generally in the range of 7.1-7.5. Suitable fibrinogen complexes can also contain fibronectin.

The fibrinogen applied to form a layer of the dressing typically has a concentration of 1 mg cm$^2$ to 60 mg/cm$^2$, e.g., at least 5, 10, 15, 20, 30, 40, 50 mg/cm$^2$. The first and second fibrinogen layers can be the same size, e.g., such that the second fibrinogen layer generally is coextensive with the first fibrinogen layer. Alternatively, the first fibrinogen layer can be noncoextensive with the second fibrinogen layer; or the second fibrinogen layer can be noncoextensive with the first fibrinogen layer. Thus, the first fibrinogen layer can be up to 100% of the size of the second fibrinogen layer, or the second fibrinogen layer can be up to 100% of the size of the first fibrinogen layer.

The thrombin employed in the hemostatic dressing can be a lyophilized mixture of human plasma proteins which have been purified and virally inactivated. The dressings of the invention typically contain thrombin at a potency of about 1 to 160 International Units (IU)/cm$^2$, e.g., at least 5, 10, 15, 20, 25, 30, 35, 40, 45, 50, 60, 70, 80, 100, 125, 150 IU/cm$^2$. Optional constituents include albumin (generally about 5 mg/mL) and glycine (generally about 0.3 M±0.05M). The pH of the thrombin is generally in the range of 6.5-7.1.

The thrombin layer is applied to the first fibrinogen layer such that it is noncoextensive with the first fibrinogen layer and/or will be noncoextensive with the second fibrinogen layer upon application of the second fibrinogen layer. For example, the thrombin layer can occupy about 5% to about 95% of the surface area of the first fibrinogen layer and/or about 5% to about 95% of the surface area of the second fibrinogen layer. The thrombin can be applied to the fibrinogen layer in a single spot or as a series of spots on the fibrinogen layer such that the total surface area of the thrombin spots occupies about 5% to about 95% of the surface area of the first fibrinogen layer and/or about 5% to about 95% of the surface area of the second fibrinogen layer.

Such a spot or spots of thrombin can have any geometric shape, e.g., filled or unfilled circles, rectangles, triangles, lines, amorphous shapes, or combinations thereof. Such spots can be applied to the first fibrinogen layer in an ordered or random pattern. A plurality of spots can form any of a variety of shapes and patterns, such as an array, a grid, a series of concentric spots (e.g., concentric circles or squares), an overlapping series of spots (e.g., overlapping circles), spokes emanating from an axis, or any other configuration, provided that the total surface area of the thrombin is about 5% to about 95% of the surface area of the first fibrinogen layer and/or about 5% to about 95% of the surface area of the second fibrinogen layer. In general, a large number of small spots is preferred over a small number of large spots. For example, a 20×20 array of spots generally is preferable over a 10×10 array of spots occupying the same total surface area. However, the spots can be of any size provided that the total surface area of the thrombin is about 5% to about 95% of the surface area of the first fibrinogen layer and/or about 5% to about 95% of the surface area of the second fibrinogen layer. For example, depending upon the overall size of the dressing, the spots can be, without limitation, at least about 0.01, 0.1, 0.5, 1, 2, 3, 4, 5, 6, 7, 8, 9, 10 mm or more in diameter, width, or length. In one embodiment, for example, 4 circular spots having a diameter of 2-3 mm each can occupy a square centimeter of a dressing. A variety of other configurations are within the scope of the invention and can readily be utilized by those skilled in the art.

The dressing can be prepared as any of a variety of sizes and shapes. Typically, the dressings are of a size and shape that can readily be handled by those skilled in the art, typically less than 12" in length along any side, e.g., 1"×1", 1"×2", 4"×4", etc. The moisture level of the dressing typically is less than 8% (e.g., less than 7, 6, 5, 4, 3, 2, or 1%).

Any of a variety of resorbable material known to those skilled in the art can be employed in the present invention. For example, the resorbable material can be a proteinaceous substance, such as fibrin, keratin, collagen and/or gelatin, or a carbohydrate substances, such as alginates, chitin, cellulose, proteoglycans (e.g. poly-N-acetyl glucosamine), glycolic acid polymers, lactic acid polymers, or glycolic acid/lactic acid co-polymers. For example, the resorbable material can be a carbohydrate substance. Illustrative examples of resorbable materials are sold under the tradenames VICRYL™ and DEXON™.

Generally, the various layers of the hemostatic dressing can be affixed to one another by any means known and available to those skilled in the art. Typically, the fibrinogen layer(s) and/or the thrombin layer(s) is (are) applied as a series of quick-frozen aqueous solution layers and subsequently lyophilized or freeze-dried, e.g., after application of each layer, and upon assembly of the entire dressing. The layers can be applied by any of a variety of techniques, including spraying, pipetting (e.g., with a multi-channel pipettor), sprinkling, using a mask, electrostatic deposition, using a microsyringe array system, or dispensing using a dispensing manifold that contains ports for producing a high density array.

In certain embodiments of the present invention, when the dressings are prepared using a mold, a release agent, such as sucrose, is applied to the mold before the first layer of the dressing is applied. In such embodiments, the hemostatic dressing further comprises a release layer, which contains said release agent.

Alternatively, a physiologically-acceptable adhesive can be applied to the resorbable material and/or the backing material (when present) and the fibrinogen layer(s) and or the thrombin layer(s) subsequently affixed thereto.

In one embodiment of the dressing, the physiologically-acceptable adhesive has a shear strength and/or structure such that the resorbable material and/or backing material can be separated from the fibrinogen layer after application of the dressing to wounded tissue. In another embodiment, the physiologically-acceptable adhesive has a shear strength such that the resorbable material and/or backing material cannot be separated from the fibrinogen layer after application of the dressing to wounded tissue.

Suitable fibrinogen and thrombin can be obtained from human or mammalian plasma by any of the purification methods known and available to those skilled in the art; from supenatants or pastes of recombinant tissue culture, viruses, yeast, bacteria, or the like that contain a gene that expresses a human or mammalian plasma protein which has been introduced according to standard recombinant DNA techniques; or from the fluids (e.g., blood, milk, lymph, urine or the like) of transgenic animals that contain a gene that expresses human fibrinogen and/or human thrombin which has been introduced according to standard transgenic techniques.

In general, the purity of the fibrinogen and/or the thrombin for use in the hemostatic dressing will be of an appropriate purity known to one of ordinary skill in the relevant art to lead to efficacy and stability of the protein. The fibrinogen and/or the thrombin can be subjected to multiple chromatographic purification steps, such as affinity chromatography and immunoaffinity chromatography, to remove substances which may cause fragmentation, activation and/or degradation of the fibrinogen and/or the thrombin during manufacture, storage and/or use. Illustrative examples of such substances that can be removed by purification include protein contaminants, such as plasminogen, inter-alpha trypsin inhibitor and pre-alpha trypsin inhibitor; non-protein contaminants, such as lipids; and mixtures of protein and non-protein contaminants, such as lipoproteins.

During use of the hemostatic dressing, the fibrinogen and the thrombin can be activated at the time the dressing is applied to the wounded tissue by the endogenous fluids (e.g., blood) of the patient escaping from the hemorrhaging wound. Alternatively, in situations where fluid loss from the wounded tissue is insufficient to provide adequate hydration of the protein layers, the fibrinogen and or the thrombin can be activated by an application of a physiologically-acceptable liquid (e.g., water, buffer, saline), optionally containing any necessary co-factors and/or enzymes, prior to or upon application of the hemostatic dressing to the wounded tissue.

In addition, one or more supplements can also be contained in one or more layers of the hemostatic dressing, e.g., drugs such as growth factors, polyclonal and monoclonal antibodies and other compounds. Illustrative examples of such supplements include, but are not limited to: antibiotics, such as tetracycline and ciprofloxacin, amoxicillin, and metronidazole; anticoagulants, such as activated protein C, heparin, prostacyclin ($PGI_2$), prostaglandins, leukotrienes, antithrombin III, ADPase, and plasminogen activator; steroids, such as dexamethasone, inhibitors of prostacyclin, prostaglandins, leukotrienes and/or kinins to inhibit inflammation; cardiovascular drugs, such as calcium channel blockers, vasodilators and vasoconstrictors; chemoattractants; local anesthetics such as bupivacaine; and antiproliferative/antitumor drugs such as 5-fluorouracil (5-FU), taxol and/or taxotere; antivirals, such as gangcyclovir, zidovudine, amantidine, vidarabine, ribaravin, trifluridine, acyclovir, dideoxyuridine and antibodies to viral components or gene products; cytokines, such as α- or β- or γ-Interferon, α- or β-tumor necrosis factor, and interleukins; colony stimulating factors; erythropoietin; antifungals, such as diflucan, ketaconizole and nystatin; antiparasitic agents, such as pentamidine; anti-inflammatory agents, such as α-1-anti-trypsin and α-1-antichymotrypsin; anesthetics, such as bupivacaine; analgesics; antiseptics; and hormones. Other illustrative supplements include, but are not limited to: vitamins and other nutritional supplements; glycoproteins; fibronectin; peptides and proteins; carbohydrates (both simple and/or complex); proteoglycans; antiangiogenins; antigens; lipids or liposomes; and oligonucleotides (sense and/or antisense DNA and/or RNA).

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference.

EXAMPLES

Example 1

The example set forth below demonstrates that delamination of the dressings can be decreased by preparing a dressing in which the thrombin layer is not coextensive with the first and second fibrinogen layers. In this example, thrombin was dispensed onto the first fibrinogen layer in either of two configurations. In the conventional dressings, the thrombin fully covered the first fibrinogen layer (this configuration is referred to herein as "full" coverage). In the dressings of the invention, the thrombin was configured on top of the first fibrinogen layer as a single circle that was not coextensive with the first fibrinogen layer (this configuration is referred to herein as "circle" coverage).

To prepare the dressings, fibrinogen was formulated in a conventional manner: 35 mg/ml of total protein (TP) in Buffer D (100 mM NaCl, 1.1 mM $CaCl_2*H_2O$, 10 mM Tris HCl, 10 mM Sodium Citrate, 2% Sucrose, 2.8 mg/ml albumin, 0.52 mg/ml TWEEN-80, pH 7.2) containing albumin at 80 mg/g of TP and polysorbate at 15 mg/g of TP. Thrombin concentrate, having a potency of 4745 IU/ml, was formulated in each of four different buffers to obtain a thrombin solution containing 2000 The four buffers are described in Table 1. The dressings were manufactured manually, and 18 dressings were produced for each of the four thrombin formulations and coverage types to produce a total of 144 dressings. The dressings were freeze-dried, packaged with desiccant, then tested in in vitro assays for appearance, moisture content, gamma dimerization, and percent clottable protein, and in an ex vivo pig arteriotomy assay.

Appearance

All dressings were tested for delamination in an appearance assay. Dressings were considered to be passing if the fibrinogen layers of the dressing were attached to each other along all four edges Delamination of the dressing layers makes the dressings difficult to handle and renders the dressings susceptible to fragmentation if surface cracks in the layers are also present As shown in Table 1, dressings in which the thrombin layer was applied with circle coverage (groups 2, 4, 6, and 8) had a higher pass rate in the delamination test (i.e., appearance test) than did dressings in which the thrombin layer was applied with full coverage (groups 1, 3, 5, and 7). While dressings made with thrombin applied with full coverage tend to fail the appearance test, nearly 100% of the dressings made with thrombin applied with circle coverage passed the appearance test

TABLE 1

| Group | Thrombin Formulation | Coverage | Appearance Pass | Moisture Content | % Dimerization clotted/ unclotted | % Clottable Protein | EVPA |
|---|---|---|---|---|---|---|---|
| 1 | 150 mM NaCl 10 mM Tris 40 mM CaCl$_2$ 100 mM Lysine | full | 7/18 | 0.96 | 95/7 | 86 | 12/12 |
| 2 | 2000 IU thrombin pH 7.5 | circle | 18/18 | 1.03 | 90/8 | 78 | 11/12 |
| 3 | 150 mM NaCl 10 mM Tris 100 mM Lysine | full | 4/6 | 1.16 | 83/8 | 99 | not tested |
| 4 | 2000 IU thrombin pH 7.5 | circle | 18/18 | 1.00 | 89/3 | 93 | 12/12 |
| 5 | 150 mM NaCl 10 mM Tris 40 mM CaCl$_2$ 200 mM Lysine | full | 0/6 | 0.90 | 90/10 | 83 | not tested |
| 6 | 2000 IU thrombin pH 7.5 | circle | 17/18 | 1.07 | 94/7 | 80 | 10/12 |
| 7 | 150 mM NaCl 10 mM Tris 200 mM Lysine | full | 3/6 | 0.89 | 92/3 | 80 | not tested |
| 8 | 2000 IU thrombin pH 7.5 | circle | 18/18 | 0.80 | 90/7 | 71 | 12/12 |

The improved resistance to delamination was observed irrespective of the buffer in which the thrombin was formulated. Thus, the removal of CaCl$_2$ from certain of the buffer formulations did not affect clot formation, even though CaCl$_2$ is required by thrombin for activation. These results indicate that there was sufficient CaCl$_2$ present in the fibrinogen formulation (1.1 mM) to promote thrombin activation. Similarly, the increase in solids content (Lysine) did not have a significant effect.

The moisture content was measured for one of the dressings from each group. The moisture content of the dressings averaged 0.98% and was very consistent throughout the groups, ranging from 0.80 to 1.16%. This moisture content level is typical for such dressings.

One dressing from each group was used to measure gamma-gamma dimerization in a conventional assay. As described by Okude et al., Biol. Pharm. Bull. 16: 448-452, a gamma-gamma dimer assay measures the ability of thrombin to cross-link the gamma chains of fibrinogen, thus forming a clot. Generally, in order to perform this assay, each dressing is ground into a uniform, fine powder in a low moisture chamber and divided into two equal portions. 500 µL 0.9% saline is added to one portion and 500 µl of Okude Dissolving Solution (ODS) (10 M Urea, 1% SDS, 0.1% β-Mercaptoethanol, 0.01% Bromophenol Blue) is added to the other. Both are vortexed briefly and incubated at 40° C. for 5 minutes. This allows clot formation in the saline sample, while the denaturing agents in ODS prevent clot formation. Both samples are suspended in 5 volumes of ODS incubated for 1 h at 40° C., dissolved in Laemmli sample buffer with β-Mercaptoethanol, and electrophoresed on SDS-PAGE gels. The gels are stained with Coomassie Blue to visualize proteins. As shown in Table 1, all dressings showed a high percentage of dimerization after clotting and a low percentage of dimerization in the non-clotted dressings, indicating that no interaction between the thrombin and fibrinogen took place during the manufacture of the dressing.

Clottable Protein

Two dressings from each group also were tested to measure the percentage of clottable protein in the dressing. In this assay, the dressing was wet and the clotted protein was sedimented by centrifugation. The elimination of CaCl$_2$ from certain of the thrombin formulations did not significantly affect clot formation. As with the dimerization assay described above, these results indicate that there was sufficient CaCl$_2$ present in the fibrinogen formulation (1.1 mM) to promote thrombin activation.

Ex Vivo Porcine Arteriotomy Dressing Performance Test

Twelve of the hemostatic dressings from certain of the groups were tested in an ex vivo porcine arteriotomy assay to determine whether the dressings can maintain adequate pressure in a simulated injury. As shown in Table 1, dressings manufactured with circle coverage, such that the thrombin layer is not coextensive with the fibrinogen layers, were able to maintain adequate pressure in this assay.

A standard ex vivo porcine arteriotomy assay can be performed as follows. Obtain frozen porcine aorta and thaw. Aortas can be thawed overnight at 4° C., or individually wrapped in the water bath at 37° C. Dissect excess connective tissue from approximately first 11 cm of the aorta. Usually, the first 5-5.5 cm are free from collateral vessels. The next 5-5.5 cm should not have more than 1-2 collaterals. These can be easily sealed or patched with cyanoacrylate glue.

Cut the aorta into two 5.5 cm pieces. Invert aorta exposing the interior using a hemostat or blunt forceps. Wash both the interior and exterior of the vessel with 1-5 mL of PBS at 37° C. Stretch an O-ring over a 20 cc syringe with an approximately 0.6 cm (0.25 in) hole drilled into one side. Using fingers or hemostats pull the vessel onto the syringe. Fit another O-ring of the same size onto the bottom.

Using curved hemostats, carefully secure both O-rings over the top of the vessel. The distance between both O-rings should be 3.5 cm. The artery should be snug fitting and held securely in place. Position the secured vessel such that the hole in the syringe lies in the middle of the distance between the O-rings.

Fill the syringe with PBS at 37° C. and place the screw through the outside of the syringe and into the plunger, so that the plunger is held in a stationary position. Wash the artery on the syringe with 1-2 ml of PBS at 37° C. Using a 16-gauge needle, make a hole in the center (approximately 1.75 cm from either O-ring) over the syringe hole. The 16-gauge needle should be replaced after every 12 uses.

Open the sealed bag containing the dressing and immediately place the dressing over the incision (approximately 0.5 cm from each O-ring, so as not to touch either O-ring). All dressings should be individually packaged prior to use.

Using a P-1000 Pipetman, wet the dressing with PBS at 37° C. For 15 mg/cm$^2$ dressings use 800 μL, and for 8 mg/cm2 dressings use 500 μL. Immediately place the syringe shield on top of the dressing, so as not to touch either O-ring. Press lightly to secure.

Place the syringe into the incubator at 37° C. using the holding box in order to keep the syringe and all its components stationary. Cover with the plastic cover, placing a 200 g weight securely over top. Assure even distribution of weight. Allow it to incubate for 5 minutes at 37° C.

Remove the syringe from the incubator. Carefully remove the shield covering the dressing. Attach the syringe to the tubing connected to a peristaltic pump. The tubing should be arranged so that it runs through the pump and is connected to a Y-junction on the opposite side. The Y-junction creates two outlets, allowing the PBS to be pumped into the syringe at one site as back pressure is being generated in the other. This back pressure is directly measured using an in-line pressure transducer-analyzer, and recorded using DMSI-200/1 software.

Pump the PBS at 37° C. into the syringe, and immediately start monitoring the pressure generated. Initiate a 30-second slow ramp (setting 4 at 1× speed for pump in E229, setting 7.5 at 1× speed for pump in E132), such that the initial flow rate is approximately 0.3 ml/min.

After the first 30 seconds, the flow rate is escalated to approximately 3 ml/min (10× speed, both settings). This should be done until a pressure of 200 mm Hg is obtained. Once 200 mm Hg is achieved, start the timer for 2 minutes.

Stop the pump once 200 mm Hg is obtained. Monitor the pressure generated. If pressure starts to drop, turn pump back on until adequate pressure is obtained. This may be done as often as necessary throughout the two-minute interval (under normal conditions, the pressure should be maintained between 200 and 215 mm Hg.). In addition, note any leakage and its location. If a leak occurs, note the maximum time and burst pressure at the moment of leakage. Judge dressing performance based on the following pass/fail criteria.

A dressing is considered passing if it maintains a fairly consistent pressure of 200 mm Hg for two minutes with absolutely no leakage. A dressing is also considered passing if it maintains a fairly consistent pressure of 200 mm Hg for two minutes with only minimal leakage (e.g., slow seeping or a leak that has resealed itself).

A dressing is considered failing if it cannot maintain adequate pressure due to severe leakage. This includes leakage caused by poor adhesion, as well as leakage due to manufacturing flaws. Dressings that may be considered as failing in this assay can nonetheless be used to treat less severe wounds.

Example 2

The data set forth below in Table 2 demonstrate that delamination can be attributed to full coverage of the thrombin layer (or buffer) on the first fibrinogen layer. Dressings that were produced with thrombin applied such that the thrombin layer was not coextensive with the first fibrinogen layer generally passed the delamination appearance test (groups 9-11 and 13-16 in Table 2). Similarly, dressings that were produced with no middle layer, i.e., having only two fibrinogen layers, generally did not become delaminated, and the fibrinogen layers adhered tightly to each other.

In this example, fibrinogen was formulated as described above, and thrombin was formulated as described in Table 2. The fibrinogen layers (approx 1.2 mL) were applied using a programmable pipette, and the dressings were manufactured manually as described herein. The middle layer of the dressing (i.e., thrombin or fibrinogen) was applied either by spraying using an air brush or by pipetting. For each formulation and method of application, four different volumes of the middle layer were applied, with 120 μl considered to be a "standard" volume. When the middle layer was applied by spraying, the spraying time was increased to increase the volume applied. Full coverage of the first fibrinogen layer was achieved with all groups in which the thrombin was sprayed. When the middle layer was applied by pipetting, full coverage of the first fibrinogen layer was obtained only when 1000 p. 1 of the middle layer was applied. Smaller volumes of the middle layer were used to demonstrate delamination is inhibited by application of the thrombin layer such that it is not coextensive with the fibrinogen layers. Six dressings were tested in each group. Group 1 was used as a control and was assessed for moisture content, gamma-gamma dimerization, percentage of clottable protein, and appearance (i.e., delamination). The control dressing demonstrated a moisture level of 1.3%, good dimerization on clotting (82%), low dimerization of the non-clotted sample (1%), and a low, but acceptable, percentage of clottable protein (68%). All of the dressings were assessed for delamination, and the number of passing dressings is shown in Table 2.

The data set forth in Table 2 show that, when the middle layer is applied with full coverage of the fibrinogen layer (groups 1-8 and 12), all of the dressings became delaminated at their edges. When partial coverage was achieved, the dressings generally passed appearance. The observation that increasing volumes of the thrombin middle layer, applied by pipette, increased the delamination of the dressing indicates that delamination is more a function of the coverage and composition of the middle layer than it is a function of the rate at which the middle layer freezes during manufacture of the dressing. Thus, dressings having a thrombin layer that is noncoextensive with the fibrinogen layers inhibit delamination.

TABLE 2

| Group | Formulation of Middle Layer | Application Method | Volume (μl) | Coverage | Appearance |
|---|---|---|---|---|---|
| 1 | 150 mM NaCl | spray | 120 | full | 0/6 |
| 2 | 10 mM Tris | | 250 | full | 0/6 |
| 3 | 40 mM CaCl$_2$ | | 500 | full | 0/6 |
| 4 | 100 mM Lysine 2000 IU thrombin pH 7.5 | | 1000 | full | 0/6 |
| 5 | 150 mM NaCl | spray | 120 | full | 0/6 |
| 6 | 10 mM Tris | | 1250 | full | 0/6 |
| 7 | 200 mM Lysine | | 500 | full | 0/6 |
| 8 | 2000 IU thrombin pH 7.5 | | 1000 | full | 0/6 |
| 9 | 150 mM NaCl | pipette | 120 | partial | 6/6 |
| 10 | 10 mM Tris | | 250 | partial | 6/6 |
| 11 | 40 mM CaCl$_2$ | | 500 | partial | 3/6 |
| 12 | 100 mM Lysine 2000 IU thrombin pH 7.5 | | 1000 | full | 0/6 |
| 13 | fibrinogen | pipette | 120 | partial | 6/6 |
| 14 | | | 250 | partial | 6/6 |
| 15 | | | 500 | partial | 6/6 |
| 16 | | | 1000 | partial | 6/6 |

OTHER EMBODIMENTS

While the invention has been described with reference to the foregoing detailed description thereof and preferred embodiments, the foregoing description is intended to illustrate and not limit the invention, which is defined by the scope of the appended claims. Other aspects, advantages, and modifications are within the scope of the following claims.

What is claimed is:

1. A hemostatic dressing which comprises:
   (i) a first fibrinogen layer;
   (ii) a thrombin layer adjacent to said first fibrinogen layer; and
   (iii) a second fibrinogen layer adjacent to said thrombin layer;
   wherein the thrombin layer is not coextensive with the first fibrinogen layer and/or the second fibrinogen layer; and
   wherein the first fibrinogen layer and the second fibrinogen layer are affixed to one another at their edges wherein the thrombin layer is coextensive with about 20% to about 50% of the first fibrinogen layer.

2. A hemostatic dressing which comprises:
   (i) a resorbable material layer;
   (ii) a first fibrinogen layer adjacent to said resorbable material layer;
   (iii) a thrombin layer adjacent to said first fibrinogen layer; and
   (iv) a second fibrinogen layer adjacent to said thrombin layer;
   wherein the thrombin layer is not coextensive with the first fibrinogen layer and/or the second fibrinogen layer; and
   wherein the first fibrinogen layer and the second fibrinogen layer are affixed to one another at their edges wherein the thrombin layer is coextensive with about 20% to about 50% of the first fibrinogen layer.

3. A hemostatic dressing which comprises:
   (i) a first fibrinogen layer;
   (ii) a resorbable material layer adjacent to said first fibrinogen layer;
   (iii) a thrombin layer adjacent to said resorbable material layer; and
   (iv) a second fibrinogen layer adjacent to said thrombin layer;
   wherein the thrombin layer is not coextensive with the first fibrinogen layer and/or the second fibrinogen layer; and
   wherein the first fibrinogen layer and the second fibrinogen layer are affixed to one another at their edges wherein the thrombin layer is coextensive with about 20% to about 50% of the first fibrinogen layer.

4. The hemostatic dressing according to any one of claims 1-3, wherein the thrombin layer is configured as an array of spots comprising thrombin.

5. The hemostatic dressing according to any one of claims 1-3, wherein the thrombin layer is configured as a single spot comprising thrombin.

6. The hemostatic dressing according to any one of claims 1-3, wherein the thrombin layer is configured as a plurality of lines comprising thrombin.

7. The hemostatic dressing according to any one of claims 1-3, further comprising a backing material.

8. The hemostatic dressing of claim 2, wherein said resorbable material is selected from the group consisting of glycolic acid polymers, lactic acid polymers and glycolic acid/lactic acid co-polymers.

9. The hemostatic dressing according to any one of claims 1-3, wherein one or more of said layers comprises a solubilizing agent.

10. The hemostatic dressing according to any one of claims 1-3, wherein one or more of said layers comprises a filler.

11. The hemostatic dressing according to any one of claims 1-3, wherein one or more of said layers comprises a binding agent.

12. A method of treating wounded tissue, which comprises applying to said wounded tissue a hemostatic dressing according to any one of claims 1-3.

13. The method of claim 12, further comprises hydrating said hemostatic dressing with a liquid that is exogenous to the wounded tissue.

14. The method of claim 12, further comprising hydrating said hemostatic dressing with a liquid that is endogenous to the wounded tissue.

15. A method for preparing a hemostatic dressing, the method comprising:
   providing a first layer of fibrinogen;
   applying a layer of thrombin to said first layer of fibrinogen; and
   applying a second layer of fibrinogen to the layer of thrombin, wherein the layer of thrombin is not coextensive with the first fibrinogen layer and/or the second fibrinogen layer wherein the thrombin layer is coextensive with about 20% to about 50% of the first fibrinogen layer.

16. A method for preparing a hemostatic dressing, the method comprising:
   providing a resorbable or nonresorbable backing layer having attached thereto a first layer of fibrinogen;
   applying a layer of thrombin to said first layer of fibrinogen on a side of the fibrinogen layer that is opposite of the side to which the resorbable or nonresorbable backing layer is attached; and
   applying a second layer of fibrinogen to the layer of thrombin, wherein the layer of thrombin is not coextensive with the first fibrinogen layer and/or the second fibrinogen layer wherein the thrombin layer is coextensive with about 20% to about 50% of the first fibrinogen layer.

* * * * *